(12) United States Patent
Jackson

(10) Patent No.: US 6,527,757 B1
(45) Date of Patent: Mar. 4, 2003

(54) UNDERGARMENT PROTECTION ARTICLE AND METHOD

(75) Inventor: Wanda W. Jackson, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 52 days.

(21) Appl. No.: 09/609,729

(22) Filed: Jul. 3, 2000

Related U.S. Application Data

(63) Continuation-in-part of application No. 09/079,745, filed on May 15, 1998, now Pat. No. 6,102,902.

(51) Int. Cl.⁷ .............................................. A61F 13/15
(52) U.S. Cl. ...................... 604/387; 604/389; 604/393; 604/385.03; 604/385.04
(58) Field of Search .................................. 604/317–402

(56) References Cited

U.S. PATENT DOCUMENTS

| | | | |
|---|---|---|---|
| 4,917,697 A | 4/1990 | Osborn, III et al. | 604/387 |
| 5,037,418 A | 8/1991 | Kons et al. | 604/387 |
| 5,087,254 A | 2/1992 | Davis et al. | 604/386 |
| 5,098,422 A * | 3/1992 | Davis et al. | 604/385.1 |
| 5,154,715 A | 10/1992 | Van Iten | 604/387 |
| 5,167,653 A * | 12/1992 | Igaue et al. | 604/385.2 |
| 5,221,275 A * | 6/1993 | Van Iten | 604/387 |
| 5,429,630 A | 7/1995 | Beal et al. | 604/385.1 |
| 5,558,663 A | 9/1996 | Weinberger et al. | 604/387 |
| 5,584,829 A | 12/1996 | Lavash et al. | 604/387 |
| 5,591,147 A | 1/1997 | Couture-Dorschner et al. | 604/369 |
| 5,591,150 A | 1/1997 | Olsen et al. | 604/385.1 |
| 5,611,879 A | 3/1997 | Morman | 156/201 |
| 5,615,691 A | 4/1997 | Huffman | 128/891 |
| 5,624,425 A | 4/1997 | Gray et al. | 604/385.2 |
| 5,628,739 A | 5/1997 | Hsieh et al. | 604/385.1 |
| 5,650,223 A | 7/1997 | Weinberger et al. | 442/62 |
| 5,704,930 A | 1/1998 | Lavash et al. | 604/385.2 |
| 5,713,885 A | 2/1998 | Jogenson et al. | 604/385.2 |
| 5,755,711 A | 5/1998 | Hammons et al. | 604/385.1 |
| 5,785,698 A * | 7/1998 | Van Iten | 604/387 |

FOREIGN PATENT DOCUMENTS

| | | | |
|---|---|---|---|
| EP | 0595047 | 5/1994 | A61F/13/15 |
| EP | 0681820 | 11/1995 | A61F/13/15 |

* cited by examiner

Primary Examiner—Jeanette Chapman
(74) Attorney, Agent, or Firm—Thomas J. Connelly; Thomas M. Parker; Douglas G. Glantz

(57) ABSTRACT

An absorbent article and method are disclosed for providing side leakage protection for an undergarment and absorbent article positioning guidance for proper placement on the undergarment. In one embodiment, an absorbent cuff pad is configured to fit the pudendal region of a woman with cuffs for receiving a crotch portion of an undergarment. In one embodiment, an absorbent pad and liquid-impermeable baffle are provided with stiffening means for a pair of garment-attachment nesting ridges for receiving an loans arcuately shaped crotch portion of an undergarment. In one embodiment, an absorbent configured to fit the pudendal region of a woman, a liquid-impermeable baffle, and stiffening means for multiple pairs of garment-attachment nesting ridges receive and protect an arcuately shaped crotch portion of an undergarment. Arcuately shaped pleats on a bottom lateral side surface of the absorbent article form the nesting ridges. In one embodiment, a pressure sensitive adhesive provides force to support the cuffs or the nesting ridges holding the undergarment in place during use. In one aspect, the absorbent article provides two or three or more garment-attachment nesting ridge pairs.

7 Claims, 5 Drawing Sheets

UNDERGARMENT PROTECTION ARTICLE AND METHOD

This is a continuation-in-part of application Ser. No. 09/079,745, filed May 15, 1998 now, U.S. Pat. No. 6,102,902.

BACKGROUND OF THE INVENTION

1. Technical Field

This invention relates to an absorbent article and method for protecting a user by absorbing or containing body fluids including menstrual fluids or other body exudates. In one aspect, this invention relates to an absorbent article and method having side leakage protection and novel means and method for positioning and fastening the absorbent article to an undergarment.

2. Background of the Invention

Many different absorbent products for the absorption of human body fluids are available in the form of feminine pads, sanitary napkins, panty shields, panty liners, and incontinence devices. Feminine care sanitary protection absorbent products absorb body fluids, including menses, and come in different functional designs. Sanitary napkins and feminine pads externally worn about the pudendal area are absorbent pads designed primarily for menstrual flow. Panty liners or panty shields are thin sanitary napkin products worn about the pudendal area for light menstrual flow. Incontinence protection absorbent products absorb body fluids including urine.

Absorbent products for the absorption of human body fluids have an absorbent positioned between a liquid-permeable body-side cover and a liquid-impermeable garment-facing baffle. These absorbent products for the absorption of human body fluids include a top layer of the liquid-permeable body-side cover, a middle layer of the absorbent, and a bottom layer of the liquid-impermeable garment-facing baffle. A pressure sensitive adhesive is secured to the baffle and used to attach the product to an inner crotch portion of an undergarment.

INTRODUCTION TO THE INVENTION

In absorbent products for the absorption of human body fluids today, a problem of leakage still persists, in that body fluids leak out at the sides of the absorbent products. Such side leakage can stain the undergarment and even the outer garments of a wearer, and such side leakage is a serious concern of the absorbent product user.

Side flaps, tabs, wings, and other side constructions, which extend from the sides of a feminine care pad, are referred to as "side flaps." Side flaps have been designed to fold onto opposite side flaps or wrap around the undergarment to provide protection from side leakage. While side flaps available today have some success in absorbing side leakage, such side flaps have certain drawbacks.

Side flaps available today are costly to manufacture as they require non-conforming shapes creating excessive trim waste.

Side flaps available today also are awkward to use. Such side flaps require careful placement within the crotch portion of the wearer's undergarment, and even then are not comfortable to the wearer. Side flaps do not maintain their position when the protective adhesive peel strip is removed from the garment-facing side of the side flaps. Many times, the side flaps then become adhered to the garment side of the baffle, or they become inadvertently and undesirably adhered or sticking to another inappropriate surface. The user then must manipulate the side flap sticking to the baffle or other inappropriate surfaces, so as to guide and position the side flaps into proper positioning prior to use. The inadvertent sticking of the side flap to the baffle or other inappropriate surfaces many times makes the article unusable. Releasing the absorbent article product from the undergarment also can be difficult and inconvenient.

Another drawback of side flaps available today has been found when many times the wearer has only a light menstrual flow and does not need the side flaps. In these situations, many customers prefer not to use the side flaps during light menstrual flow because of their many drawbacks.

Absorbent products attached to an adjacent undergarment should be held stationary during use. Absorbent products, such as sanitary napkins, overnight pads, panty liners, incontinent garments, and even some underarm shields, are attached to an adjacent garment or undergarment for positioning and support. Pressure sensitive adhesives provide the means and method for affixing the absorbent product to an adjacent garment or undergarment. The pressure sensitive adhesive is applied to the garment-facing surface of the absorbent product and is covered temporarily by a releasable peel strip until the absorbent product is placed into use.

In pressure sensitive adhesive applied to the garment-facing surface of the absorbent product today, certain drawbacks have been found to persist. The cost of the adhesive and the releasable peel strip increase the overall cost of the absorbent product. Also, special equipment and extra steps are required during the manufacturing of adsorbent products to apply the pressure sensitive adhesive and then to center and apply the releasable peel strip over the adhesive. The adhesive also can be a nuisance when it sticks to the inner surface of an undergarment, and when it leaves a tacky residue after the absorbent product is removed. The tacky residue is uncomfortable to the wearer, and the build up of the tacky residue produces a stain and eventually may ruin the undergarment. Further drawbacks are found in that it is difficult to reposition the absorbent product in the undergarment, e.g., in the manner of repositioning side flaps, after the adhesive has been attached to an inappropriate surface of the undergarment or other inappropriate surface.

Accordingly, there is a need for an absorbent article and method which provide side leakage protection, which prevent staining of undergarments and outer garments, and which provide a lower cost to produce, with lower manufacturing costs and lower material production costs. An absorbent article and method also are needed which provide accurate positioning and convenient placement of the absorbent article onto the undergarment. An absorbent article and method also are needed which provide the user with a sense of comfort during use over a variety of situations, including in one aspect, when full absorbency is not needed, yet without sacrificing the full benefits of full leakage protection, convenience of positioning and application, and wearer comfort.

It is an object of the present invention to provide an absorbent article capable of absorbing and containing menstrual fluids and/or other body exudates.

It is another object of the present invention to provide an absorbent article and method for protecting the undergarment of a wearer from side leakage.

It is another object of the present invention to provide an absorbent article and method for guiding the absorbent article into proper placement onto the undergarment of a wearer.

Another object of this invention is to provide an absorbent article and method for holding the absorbent article in proper position on the undergarment of a wearer.

Another object of the present invention is to provide a sanitary napkin or panty liner or panty shield having manufacturing cost advantages.

It is an object of the present invention to provide a sanitary napkin or panty liner or panty shield having cost of material advantages.

A further object of the present invention is to provide a sanitary napkin or panty liner or panty shield which uses less material.

It is an object of the present invention to provide an absorbent article which is more convenient to use.

It is an object of the present Invention to provide an absorbent article which is more comfortable to wear.

These and other objects and advantages of the present invention will become more apparent to those skilled in the art in view of the following detailed description and the accompanying drawings.

SUMMARY OF THE INVENTION

Briefly, the present invention provides an absorbent article and method incorporating, in one embodiment, stiffening means in arcuately shaped pleats on a bottom lateral side surface of a liquid-impermeable baffle, forming stiffened nesting ridges for protecting an undergarment from side leakage and for guiding the absorbent article into position for proper placement on the undergarment.

In one embodiment, the present invention provides an absorbent article and method incorporating cuff pad means on a bottom lateral side surface of the liquid-impermeable baffle forming cuffs for protecting an undergarment from side leakage and for guiding the absorbent article into position for proper placement on the undergarment.

An absorbent configured to fit the pudendal region of a woman and a liquid-impermeable baffle are provided with a pair of stiffened garment-attachment nesting ridges, in one embodiment, or cuffs, in one embodiment, for receiving an arcuately shaped crotch portion of an undergarment.

Arcuately shaped pleats on a bottom lateral side surface of the liquid-impermeable baffle form the nesting ridges. In one embodiment, a pressure sensitive adhesive in each nesting ridge provides force to support the nesting ridge holding the undergarment in place during use. In one aspect, the absorbent article provides two, three, or more garment-attachment nesting ridge pairs. In one aspect, the arcuately shaped pleats are formed by a polyethylene/polypropylene bi-component web material.

The article and method of the present invention include providing an absorbent designed to be attached to the crotch portion of an undergarment and having a body-side surface and an opposite garment-facing surface. A liquid-impermeable baffle is positioned adjacent to at least a portion of the garment-facing surface of the absorbent, and a liquid-permeable cover is positioned adjacent to at least a portion of the body-side surface of the absorbent. The cover and baffle cooperate to enclose the absorbent and form a pad having a pair of longitudinally oriented side edges and a pair of distally spaced ends. A garment-adhesive strip is secured to the garment-facing surface of the pad and is positioned along the longitudinal axis of the pad. A pair of nesting ridges are positioned along the longitudinal axis of the pad and are configured to provide positioning guidance and support to the wearer for placing and holding the absorbent onto the undergarment. The nesting ridges are configured to prevent staining of the crouch portion of the undergarment or outer garments. In one aspect, multiple pairs of nesting ridges are provided to accommodate varying crotch widths of the undergarment.

In one embodiment, a stiffening member of the nesting ridges is provided as part of the absorbent of the pad.

In one aspect, the absorbent article of the present invention includes an absorbent having a first sheet surface and an opposite second sheet surface, the first sheet surface having a length and a width configured to fit the pudendal region of a woman. A liquid-permeable cover is secured to the first sheet surface. A liquid-impermeable baffle is secured to the second sheet surface, the baffle having a length and a width covering the second sheet surface. A means for garment attachment includes a garment-attachment adhesive for securing the liquid-impermeable baffle to an inside surface of a crotch of an undergarment and a releasable peel strip covering the garment-attachment adhesive. Nesting ridges on the underside of the absorbent article are formed of pleats positioned to guide the absorbent article into proper placement on a wearer's undergarment and hold the absorbent article in proper placement on a wearer's undergarment during use.

A method of positioning and holding an absorbent article includes the steps of providing an absorbent article having a liquid-permeable cover sheet, an absorbent, and a garment-attachment adhesive, the adsorbent having a length and a width configured to fit the pudendal region of a woman; and positioning the absorbent article onto an undergarment by placing the edges of the undergarment into a pair of nesting ridges formed on the underside of the absorbent article. The nesting ridges are formed from pleats in the underside of the absorbent article.

DETAILED DESCRIPTION

Figure 1:
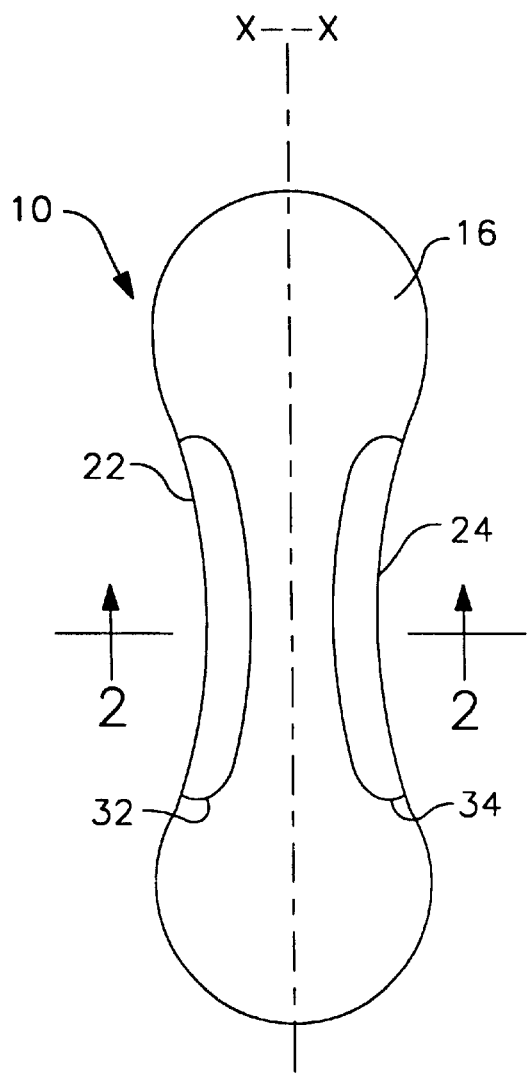
FIG. 1 is a bottom view of an absorbent article of the present invention.
Figure 2:
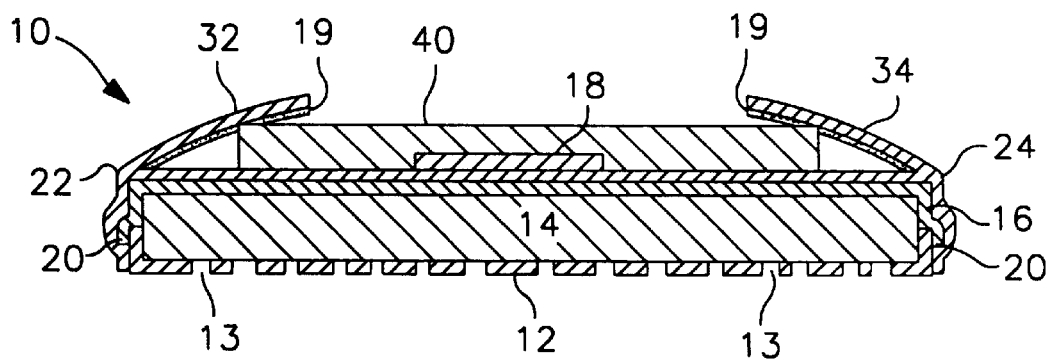
FIG. 2 is a cross sectional view, taken along line 2—2 of FIG. 1, of an absorbent article of the present invention attached to a crotch portion of an undergarment.

Referring now to FIGS. 1 and 2, an absorbent article 10 is shown as a feminine care sanitary napkin. The article and method of the present invention also have application to other absorbent article embodiments, such as a panty liner or a panty shield, an incontinent garment, a urinary shield, or an underarm pad. For purposes of illustration, the absorbent article 10 will be described as a sanitary napkin or feminine care sanitary protection pad.

The absorbent article 10 is depicted having a liquid-permeable cover 12, an absorbent 14, and a liquid-impermeable baffle 16. The absorbent 14 is positioned between the liquid-permeable cover 12 and the liquid-impermeable baffle 16. The absorbent article 10 is constructed to form layers of the liquid-permeable cover 12, the absorbent 14, and the liquid-impermeable baffle 16, vertically arranged.

The liquid-permeable cover 12 is made of a material designed to serve functionally as the material which will come into contact with a wearer's body. The liquid-permeable cover 12 is made from a woven or non-woven, natural or synthetic material which is readily penetrated by body fluids. Thermoplastic polymer films made from fibers or filaments of polyethylene or polypropylene are preferred for cover. 12.

Cover 12 has apertures 13 formed in the cover 12 to increase the rate at which the body fluids penetrate through the cover 12 into the absorbent 14.

The absorbent 14 is hydrophilic and is made of cellulose fibers, wood pulp, regenerated cellulose, cotton fibers, or a blend of pulp and other fibers. The absorbent 14 usually is resilient for enabling the absorbent article 10 to bend easily without excessive distortion. Hydro colloidal material, commonly referred to as super absorbents, can be added to the hydrophilic material to increase the absorption capacity of the absorbent article 10.

The absorbent article 10 provides service as a sanitary napkin, a panty liner, or a panty shield pad, and comes into attachment to the inside surface of a crotch portion of an undergarment 40. Undergarment 40 most often is a fabric panty having an elastic waist and leg openings separated by fabric material defining the crotch. The liquid-impermeable baffle 16 of the absorbent article 10 faces the inner surface of the crotch portion of the undergarment 40 and can be designed to permit the passage of air or vapor out of the absorbent article 10 while blocking the passage of body fluid.

A garment adhesive 18 is placed in the center of the underside of the absorbent article 10 of the present invention.

The baffle 16 can be made from a polymeric film such as polyethylene, polypropylene, or cellophane, or can be made from a bi-component film. One such material is ethyl-vinyl-acetate/polyethylene co-extruded film. In one aspect, the baffle 14 can be constructed from a liquid-permeable material that has been treated or coated to become liquid-impervious.

The cover 12 and the baffle 16 can be attached or joined together, such as by a peripheral seal 20, to enclose the absorbent 14. The cover 12 can be wrapped entirely about he absorbent 14, and then the baffle 16 can be attached to the lower surface of the cover 12 by end seals (not shown).

The absorbent article 10 usually has an overall length of between about 6 to 12 inches (15 to 30 cm) and a width of between about 2 to 3.5 inches (5 to 9 cm), sometimes about 1.5 to 3.5 inches (4 to 9 cm). The thickness of absorbent article 10 can vary form about 2 mm to about one inch (2.5 cm).

The absorbent article 10 has a first side 22 and a second side 24 longitudinally extending along a longitudinal axis X—X of the absorbent article 10. The first side 22 is situated on one side of the absorbent article 10 width as viewed relative to the longitudinal axis X—X, and the second side 24 is situated on the other side of the width of the absorbent article 10, opposite to the first side 22.

The first side 22 and the second side 24 of the absorbent article 10 have a ridge 32 and a ridge 34, respectively, positioned and extending along the width of absorbent article 10.

Ridge 32 and ridge 34 provide a nesting groove or nesting ridge for garment attachment to a lower surface 36 of the absorbent article 10. In one aspect ridge 32 and ridge 34 can be made to be a part of the baffle 16.

Ridge 32 and ridge 34 provide a nesting groove or nesting ridge formed by folds created on the underside of absorbent article 10. The folds of ridge 32 and ridge 34 are grooves or slots where the crotch of undergarment 40 may nest in a manner to be protected from body fluid staining.

In one aspect, a small amount of adhesive 19 is placed in the nesting ridges 32 and 34 of the present invention for additional security in holding the crotch width of the panty 40.

When the absorbent article 10 is positioned in the crotch portion of an undergarment 40, the wearer simply allows the undergarment to insert into ridge 32 on one side, and into ridge 34 on the other side, of the absorbent article 10. The wearer then pulls the undergarment 40 up about her torso, and the absorbent article 10 will contact and conform to her body. The body forces exerted on the absorbent article 10 operate to force or to nest the undergarment 40 into ridge 32 on one side, and into ridge 34 on the other side, of the absorbent article 10.

The nesting ridges 32 and 34 are arcuately shaped to conform to the arcuate shape of an undergarment, such as the arcuate shape of the side of crotch portion of a panty. In another embodiment, the nesting ridges of the present invention can be linear rather than arcuately shaped.

The nesting ridges 32 and 34 of the absorbent article 10 of the present invention include folds formed on a thin layer of absorbent material laminated to the baffle 16 of the absorbent article 10 of the present invention. Alternatively, the nesting ridges 32 and 34 of the absorbent article 10 of the present invention include folds formed on a thin layer of other stabilizing material such as treated paper or non-woven laminated to the baffle 16 of the absorbent article of the present invention. By thin layer is meant a layer having a thickness of about 0.01 to 0.1 inch (0.25 to 2.5 mm).

The baffle 16 of the absorbent article of the present invention can be made with a heavy weight baffle which is sufficiently thick and stiff alone, i.e., without the thin layer of absorbent material or other stabilizing material, to form the folds 32 and 34 capable of holding a panty elastic of the crotch width of the undergarment 40 held by the absorbent article 10 of the present invention. Such a heavy weight baffle 16 has a thickness of at least about 2 mils up to about 6 mils to provide the stiffness needed in the folds 32 and 34 capable of holding the panty elastic of the crotch width of the undergarment 40 held by the absorbent article 10 of the present invention.

In one aspect, the folds 32 and 34 may be provided by adding a stiffening piece or other stabilizing material, such as a cardboard or poster board having a thickness of about 0.01 to 0.1 inch (0.25 to 2.5 mm) at a board weight of about 0.1 to 0.3 gm/in$^2$ (1.5 to 5 gm/mm$^2$). The baffle 16 can be pleated with the stabilizing material trimmed in an arcuate shape to conform to the crotch of a wearer.

In a preferred embodiment, baffle 16 is laminated to a polyethylene/polypropylene bi-component web material formed to provide pleats to provide the nesting ridges 32 and 34 of the absorbent article 10 of the present invention. The polyethylene/polypropylene bi-component web material is pleated to form the folds forming the nesting ridges 32 and 34 of the absorbent article 10 of the present invention. The pleated polyethylene/polypropylene bi-component web material is put in an oven at about 265 degrees F to set the pleats 32 and 34. Pleats 32 and 34 formed from the polyethylene/polypropylene bi-component web material have been found to be comfortable to the wearer when serving as the absorbent article 10 of the present invention.

The nesting ridges 32 and 34 of the absorbent article 10 of the present invention must resist the force of the panty 40 and stay folded. It is also important that the absorbent article 10 of the present invention provide comfortable wear to the user.

In a preferred embodiment, the nesting ridges 32 and 34 of the absorbent article of the present invention resist the force of the panty and stay folded, provide comfortable wear to the user, and also are composed of an absorbent material, such as wood pulp with binder, so as to absorb body fluids.

In a preferred embodiment, the nesting ridges 32 and 34 of the absorbent article of the present invention resist the force of the panty and stay folded, provide comfortable wear to the user, and also include a friction-enhancing material, such as a latex or a rubberized material having a high co-efficient of friction, to reduce the sliding of the panty elastic or fabric in the nesting groove, thereby to reduce twisting and shifting of the undergarment.

Figure 3:
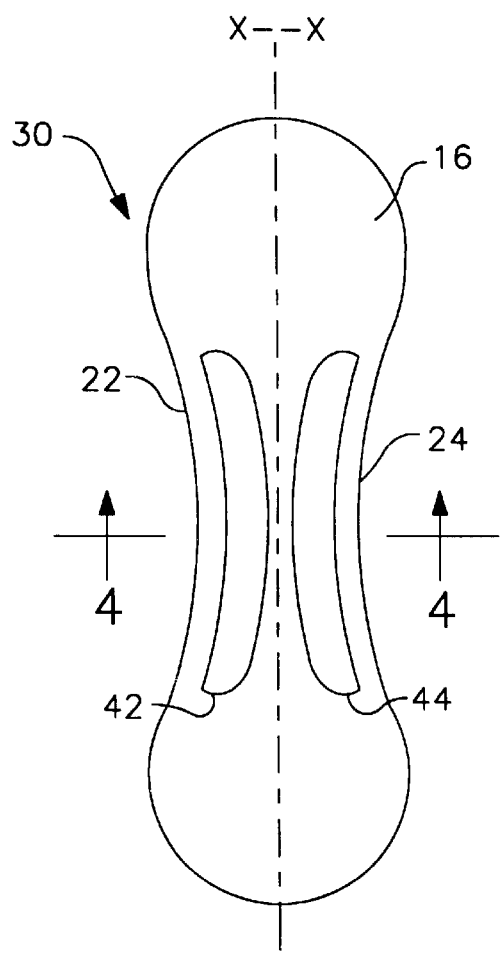
FIG. 3 is a bottom view of an absorbent article of the present invention.
Figure 4:
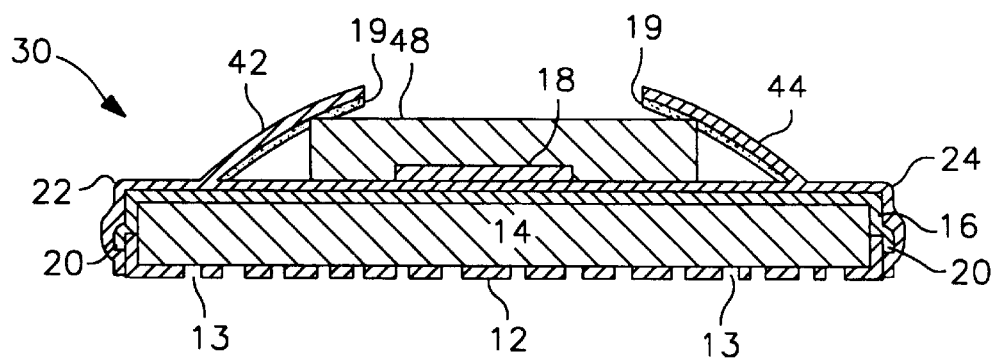
FIG. 4 is a cross sectional view, taken along line 4—4 of FIG. 3, of an absorbent article of the present invention attached to a crotch portion of an undergarment.

Referring now to FIGS. 3 and 4, an absorbent article 30 of the present invention is shown having nesting ridges 42 and 44. Nesting ridges 42 and 44 are positioned more toward the center of absorbent article 30 to accommodate a crotch portion of a panty 48 which is more narrow than the crotch portion of panty 40 as shown in FIG. 2.

Figure 5:
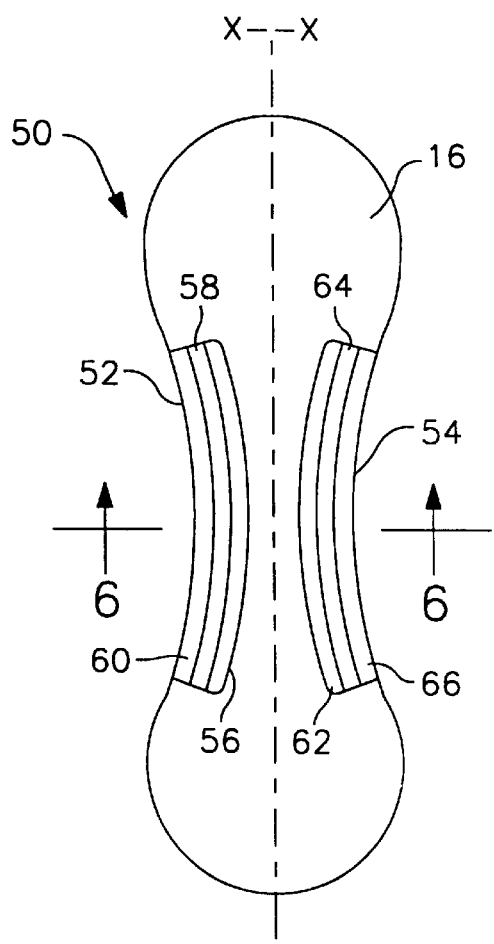
FIG. 5 is a bottom view of an absorbent article of the present invention.
Figure 6:
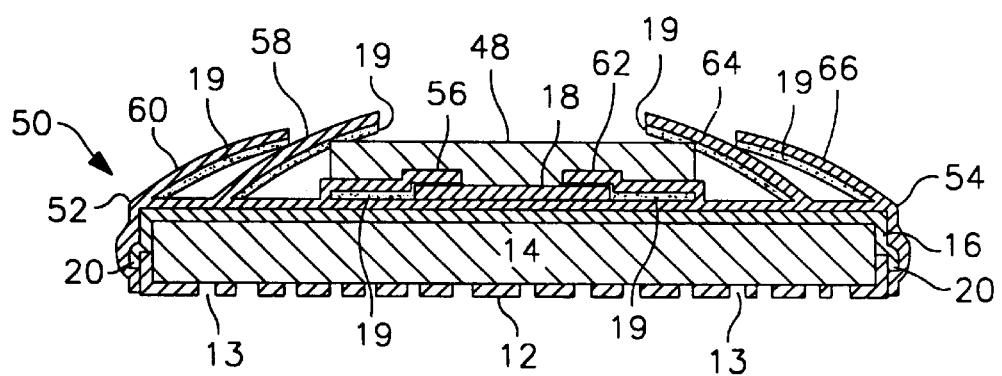
FIG. 6 is a cross sectional view, taken along line 6—6 of FIG. 5, of an absorbent article of the present invention attached to a crotch portion of an undergarment.

Referring now to FIGS. 5 and 6, an absorbent article 50 has a first side 52 and a second side 54 longitudinally extending along a longitudinal axis X—X. The first side 52 is situated on one side of the absorbent article 50 width as viewed relative to the longitudinal axis X—X of the absorbent article 50, and the second side 54 is situated on the other side of the width of the absorbent article 50, opposite to the first side 52.

Nesting ridges 56, 58, and 60 are provided of the first side 52, and nesting ridges 62, 64, and 66 are provided on the second side 54 of the absorbent pad 10. Nesting ridges 56, 58, and 60 and nesting ridges 62, 64, and 66 provide multiple pairs of nesting ridges created to allow for the comfortable accommodation of various crotch widths of the undergarment 48. For example, nesting ridges 56 and 62 provide a nesting ridge pair, e.g., a pair of nesting grooves or nesting ridges, for accommodating a crotch width of the undergarment 48 which is less than will be accommodated by nesting ridges pair 58 and 64. Nesting ridges 60 and 66 provide a nesting grooves pair or nesting ridges pair for a large crotch width. Nesting ridges 56 and 62 are shown folded flat under undergarment 48 because undergarment is larger than nesting ridges 56 and 62. The undergarment 48 is held by the intermediate nesting ridge pair provided by nesting ridges pair 58 and 64.

The nesting ridges of the absorbent article of the present invention include folds which are contoured to follow the shape of a panty crotch so that the undergarment lies smooth with no bunching. The nesting ridges of the absorbent article of the present invention also assist in keeping the absorbent article in position during wear.

Garment adhesive 18 is placed in the center of the underside of the absorbent article of the present invention. In one aspect, a small amount of adhesive 19 is placed in the nesting ridges 56, 58, and 60 and nesting ridges 62, 64, and 66 of the present invention for additional security in holding the panty 48 and other panties of smaller or larger crotch widths.

Figure 7:
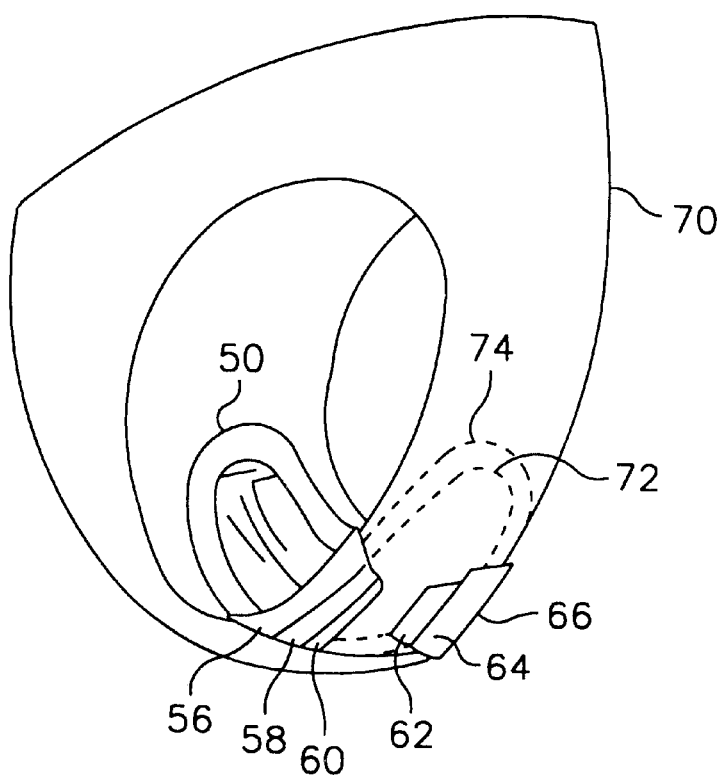
FIG. 7 is a perspective view of an absorbent article of the present invention attached to a crotch portion of an undergarment.
Figure 8:
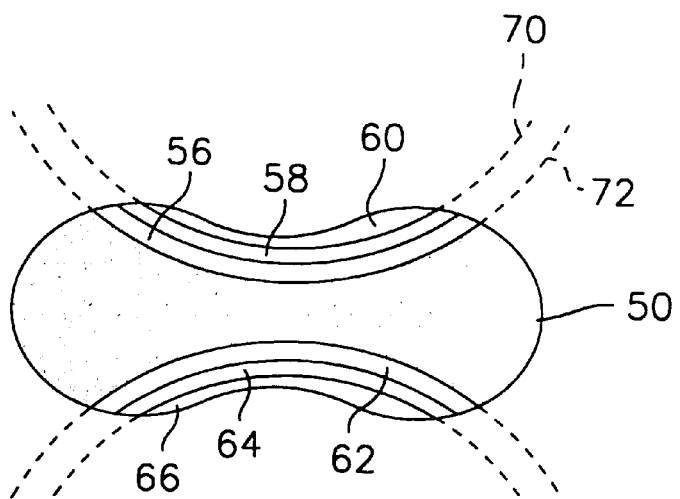
FIG. 8 is a bottom view of an absorbent article of the present invention attached to a crotch portion of an undergarment.

Referring now to FIGS. 7 and 8, an absorbent article 50 is shown securely fastened to the crotch portion of an undergarment 70. Nesting ridges 56, 58, and 60 and nesting ridges 62, 64, and 66 provide multiple pairs of nesting ridges created to allow for the comfortable accommodation of various undergarment crotch widths. For example, nesting ridges 56 and 62 provide a nesting ridge pair, e.g., a pair of nesting grooves or nesting ridges, for accommodating an undergarment crotch width 72 which is less than an undergarment crotch width 72 which will be accommodated by nesting ridges pair 58 and 64. Nesting ridges 60 and 66 provide a nesting grooves pair or nesting ridges pair for a large crotch width 70 of undergarment 70.

Figure 9:
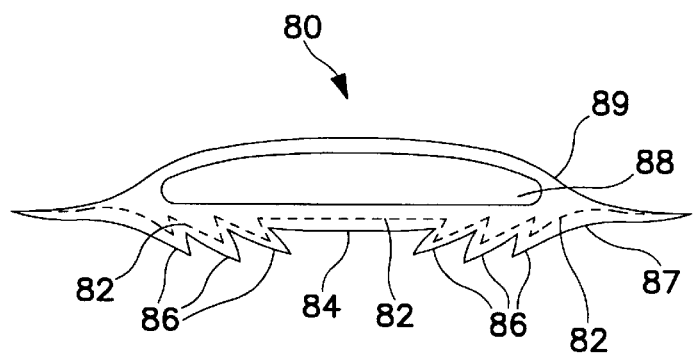
FIG. 9 is a cross sectional view of an absorbent article of the present invention incorporating stiffening means.

Referring now to FIG. 9, an absorbent article 80 of the present invention is shown incorporating stiffening means 82.

Stiffening means 82 are added to the garment-facing side 84 of the article 80 to hold the nesting ridges 86 in baffle 87 securely to the undergarment elastic edge. The stiffener means 82 are placed in such a way so as not to be noticeable unless and until the wearer engages the nesting ridges 86 as side protection elements.

Stiffening means 82 are composed of stiffening materials of heavy basis weight paper placed adjacent to baffle to facilitate creasing and maintain shape during wear, densified pulp layer, or high basis weight nonwoven web made from continuous filaments or staple fibers with binder.

The absorbent article 80 of the present invention has absorbent pad 88 and cover 89.

Figures 10, 11:
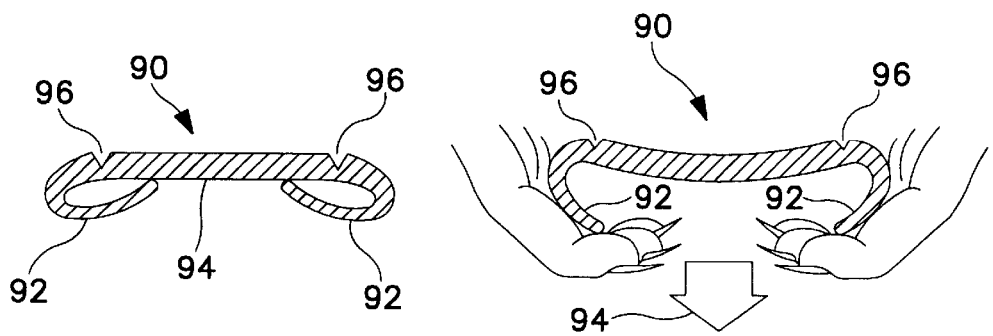
FIG. 10 is an elevational view of an absorbent article of the present invention incorporating cuffs.
FIG. 11 is a perspective view of an absorbent article of the present invention incorporating cuffs to be attached to a crotch portion of an undergarment.

Referring now to FIG. 10, an absorbent article 90 of the present invention is shown having cuffs 92.

A pair of pre-formed "cuffs" 90 are incorporated into a garment-facing side 94 of the article 90 of the present invention.

FIG. 11 is a perspective view of the absorbent article 90 of the present invention incorporating cuffs 92 to be attached to a crotch portion of an undergarment.

Figure 12:
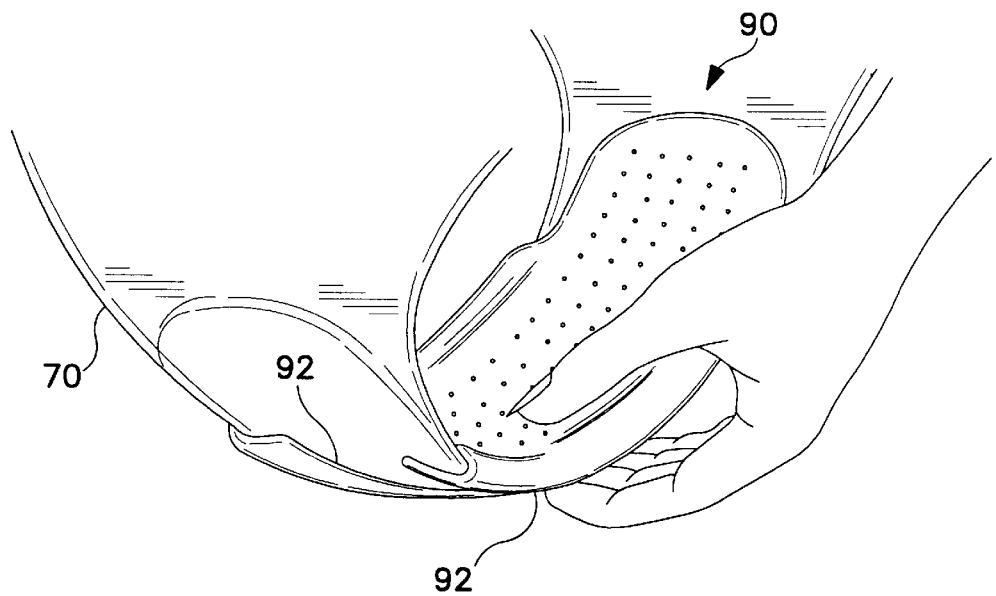
FIG. 12 is a perspective view of an absorbent article of the present invention incorporating cuffs as it s attached to a crotch portion of an undergarment.

FIG. 12 is a perspective view of an absorbent article 90 of the present invention incorporating cuffs 92 as it is attached to a crotch portion of an undergarment 70. An undergarment elastic leg opening edge is tucked into the pre-formed cuffs 92 on the garment-facing side 94 of the article 90 of the present invention to protect the undergarment 70 from staining.

The cuffs 92 of the present invention are made of a material with sufficient stiffness to hold the garment elastic in place but not so stiff as to be noticeable or uncomfortable to wear.

The cuffs 92 of the present invention are formed from thermoplastic materials which are heat set to maintain a given shape. In one aspect, the cuffs 92 of the present invention are composed of foam materials, densified pulp, nonwoven webs with fiber or latex bonding, or material with sufficient structural properties to take and maintain the preferred shape.

The novel pre-shaped cuff pads 90 of the article of the present invention provide preferred protection by staying in place. Wings offer security, but can be uncomfortable and can stick to the wearer. Now, the novel pre-shaped cuff pads 90 of the present invention stay in place securely. The cuff 92 incorporated into the novel pre-shaped cuff pads 90 of the present invention automatically wraps over the sides of a wearer's panties and anchors securely, without sticking to the wearer or to itself. The user bends the pad 90 to open the cuff 92, positions it on the panty, and then releases. The pre-shaped material holds a pre-shaped form to stay secure, yet it is soft enough to provide preferred comfort. The novel shape and a pair of side channels 96 protect against leaks. The protection and security are provided by the pre-formed "cuffs" 92 attached to a garment-facing side of an article of the present invention without the hassle of adhesive.

In accordance with the article and method of the present invention, cuffs on the absorbent article of the present invention provide shelter where the panty crotch fabric may hold, protected from staining.

In accordance with the article and method of the present invention, folds on the underside of the absorbent article of the present invention form ridge grooves or slots where the panty crotch fabric may nest, protected from staining.

In accordance with the article and method of the present invention, the panty elastic is placed between the folds of a cuff or a nesting ridge on each side of the absorbent article of the present invention. In this way, the panty elastic and the crotch portion of the panty itself are held out of the way of body fluid contact. The panty crotch is gathered between the protective folds of the cuffs or nesting ridges on the underside of the absorbent article of the present invention.

In accordance with the article and method of the present invention, the panty is automatically placed into position on the absorbent article of the present invention when it is placed between the folds of a cuff or a nesting ridge on each side. The article and method of the present invention overcome the problems and drawbacks in respect to positioning of side flaps available commercially today, and in respect to positioning and repositioning an absorbent article attached and positioned by adhesive.

The present invention provides an article and method for guiding, positioning, and holding an absorbent pad in position on a wearer's undergarment, and protecting the undergarment from side leakage staining of body fluids. The method includes pulling the absorbent article of the present invention up against a panty, and allowing the nesting ridges to receive the panty elastic or fabric of the edge of the panty crotch width into the arcuately shaped nesting ridges. The cuffs or the nesting ridges receive and hold the panty elastic or panty fabric in position and protect the panty fabric from staining.

The absorbent pad as used in the absorbent article of the present invention can be formed in the shape of a race track or oval or the like. The absorbent article pad can have other shapes, e.g., such as rectangular shapes other than oval or race track shape, provided that the shapes are designed to cover the pudendal region of a woman. The absorbent pad can be viewed as having a central longitudinal axis X—X. Most absorbent pad articles, such as sanitary napkins and panty liners or shields, are layered in sheets which are longer than they are wide. In addition to the absorbent 14 and the liquid-permeable cover 12, other layers also can be utilized, such as a transfer layer, a layer of anhydrous deodorant material, a layer containing super-absorbent materials, and additional absorbent layers.

The various layers can be vertically stacked, assembled, laminated, and/or bonded together to form the sheet or web of material from which the articles are later cut or stamped out, prior to attachment of the liquid-impermeable baffle of the present invention. The various layers can be bonded together by using heat, pressure, heat and pressure, adhesive, hot melt glue, stitching with thread, ultrasonic bonding, mechanical bonding, thermal bonding, chemical bonding, or a combination of these and/or other means known to those skilled in the art.

The liquid-impermeable baffle 16 can be designed to permit the passage of air or vapor out of the absorbent articles while blocking the passage of body fluid. The liquid-impermeable baffle 16 can be made from any material having these properties. The liquid-impermeable baffle also can be constructed from a material that will block the passage of vapor as well as fluids, if desired. A good material from which the liquid-impermeable baffle 16 can be constructed is a micro-embossed, polymeric film, such as polyethylene or polypropylene. Bi-component films can also be used. A preferred material is polyethylene film. Most preferably, the polyethylene film will have a thickness in the range of from about 0.5 mil to about 2.0 mil.

Construction adhesive can be used in the absorbent articles of the present invention to attach and bond the various layers together. For example, referring to FIGS. 2, 4, and 6 construction adhesive can be used to bond the liquid-impermeable baffle 16 to the absorbent 14 or to bond the absorbent 14 to the liquid-permeable cover 12. The presence of such construction adhesive and the amount used will depend upon manufacturing specifications. Useful construction adhesives are commercially sold by National Starch and Chemical Company, having an office located at 10 Finderne Ave., Bridgewater, N.J. 08807.

The liquid-permeable cover 12 is designed to contact the body of the wearer and can be constructed of a woven or non-woven material which is easily penetrated by body fluid. The liquid-permeable cover 12 also can be formed from either natural or synthetic fibers. Suitable materials include bonded carded webs of polyester, polypropylene, polyethylene, nylon, or other heat-bondable fibers. Other polyolefins, such as copolymers of polypropylene and polyethylene, linear low-density polyethylene, finely-perforated film webs and net materials, also work well. A preferred material is a composite of an apertured thermoplastic film positioned above a non-woven fabric material. Such a composite material can be formed by extrusion of a polymer onto a web of spunbond material to form an integral sheet. One example of this material is an apertured, thermoplastic polyethylene film bonded to a spunbond material. Spunbond material is a non-woven material which is manufactured and commercially sold by Kimberly-Clark Corporation having an office located at 401 N. Lake Street, Neenah, Wis. 54956. The apertured film/non-woven laminate exhibits a smooth appearance and is soft to the touch. This material is soft and does not irritate the wearer's skin and yet has a cushioned feel because of its bulk. Another material useful as the liquid-permeable cover 12 is a spunbond web of polypropylene. This spunbond web can contain from between about 1 percent to about 6 percent of a whitening agent, such as titanium dioxide ($TiO_2$) or calcium carbonate ($CaCO_3$) to give it a clean, white appearance. A uniform thickness of spunbond is desirable because it will have sufficient strength, after being perforated, to resist being torn or pulled apart during use. The most preferred polypropylene webs have a basis weight of between about 18 grams per square meter (g/m$^2$) to about 40 g/m$^2$. An optimum weight is between about 30 g/m$^2$ to about 40 g/m$^2$.

The absorbent layer 14 can be present as a single layer or as two or more distinct layers. The absorbent layer 14 can be formed from various natural or synthetic fibers such as wood pulp fibers, virgin cellulose fibers, regenerated cellulose fibers, cotton fibers, peat moss, or a blend of pulp and other fibers. The absorbent layer 14 also could be formed from a fine pore fabric such as wet-laid, air-dried tissue or from an uncreped through air-dried (UCTAD) tissue having a basis weight of from about 30 g/m$^2$ to about 120 g/m . The UCTAD tissue can be prepared by a process disclosed in U.S. Pat. No. 5,048,589 issued to Crook et al. on Sep. 17, 1991. The UCTAD tissue is disclosed in U.S. Pat. No. 5,399,412 issued to Sudall et al. on Mar. 21, 1995. Each of these patents is incorporated by reference and made a part hereof. The absorbent layer 14 also may be comprised of other well-known materials such as cellulose fibers, rayon fibers, cellulose sponge, hydrophilic synthetic sponge, for example polyurethane, and the like.

The absorbent articles 10, 30, 50, 80, and 90 also include one or more elongated strips or areas of a garment attachment adhesive 18, for example, referring to FIGS. 2, 4, and 6, secured to the bottom surface of the liquid-permeable baffle 16. The garment attachment adhesive 18 functions to attach the absorbent articles 10, 30, 50, 80, and 90 to the inner crotch portion of the undergarment 40, 48, or 70 during use. The garment attachment adhesive 18 provides more force in support of nesting ridges of the present invention to hold the sanitary napkin or panty liner properly aligned and retained relative to the user's vaginal opening so that maximum fluid protection can be obtained. The garment attachment adhesive 18 can cover a portion of the bottom surface of the liquid-impermeable baffle 16. The garment attachment adhesive 18 can consist of a swirl pattern of adhesive or be one or more strips of adhesive or various other patterns. The garment attachment adhesive 18 also can consist of a plurality of adhesive dots which are randomly or uniformly arranged on the exterior surface of the baffle 16. When in strip form, e.g., by way of example, in a single wide strip, the garment attachment adhesive 18 can be aligned along the central longitudinal axis X—X of the absorbent articles 10, 30, 50, 80, and 90, respectively. Alternatively, the garment attachment adhesive 18 can be present as two or more spaced apart longitudinal strips. The garment attachment adhesive 18 is of such a nature that It will allow the user to remove the absorbent article 10, 30, 50, 80, and 90 and reposition it on her undergarment if needed. A hot melt adhesive which works well as the garment attachment adhesive is commercially sold by National Starch and Chemical Company having an office located at 10 Finderne Avenue, Bridgewater, N.J. 08807.

In order to protect the garment attachment adhesive 18 from contamination or drying prior to use, the adhesive 18 can be protected by a releasable peel strip. The release strip can be a white Kraft paper which is coated on one side so that it can be released from the adhesive 18. The coating can be a silicone coating, such as a silicone polymer commercially available from Akrosil having an office located at 206 Garfield Avenue, Menasha, Wis. 54952. The release strips can be removed by the user prior to attachment of the absorbent articles 10, 30, 50, 80, and 90, respectively, to the inner crotch portion of her undergarment 40, 48, or 70, respectively.

Now, an absorbent article and method have been developed which provide a sanitary napkin or panty liner with side leakage protection, which prevent staining of undergarments and outer garments, and which provide lower cost to produce, with lower manufacturing costs and lower material production costs. The feminine sanitary protection article and method of the present invention provide accurate positioning and convenient placement of the absorbent article onto the undergarment. The feminine sanitary protection article and method provide the user with a sense of comfort during use over a variety of situations, including when full absorbency is not needed, yet without sacrificing the full benefits of full leakage protection, convenience of positioning and application, and wearer comfort.

While the invention has been described in conjunction with several embodiments, it is to be understood that many alternatives, modifications, and variations will be apparent to those skilled in the art in light of the foregoing description. Accordingly, this invention is intended to embrace all such alternatives, modifications, and variations which fall within the spirit and scope of the appended claims.

What is claimed is:

1. An absorbent article, comprising:

(a) an absorbent having a top sheet surface and an opposite bottom sheet surface, said top sheet surface having a length and a width configured to fit the pudendal region of a woman;

(b) a liquid-impermeable baffle adjacent to said bottom sheet surface, said baffle having a length and a width covering said bottom sheet surface;

(c) a pair of garment-attachment nesting ridges, each nesting ridge positioned on said liquid-impermeable baffle for receiving a side surface of a crotch portion of an undergarment, said undergarment having an undergarment elastic edge; and (d) stiffening means for holding said nesting ridges securely to said undergarment elastic edge.

2. The absorbent article of claim 1, wherein said stiffening means is positioned to be not noticeable unless and until the wearer wishes to engage the nesting ridges as side protection elements.

3. The absorbent article of claim 1, wherein said stiffening means is composed of a material selected from the group consisting of heavy basis weight paper placed adjacent to said baffle to facilitate creasing and maintain shape during wear, a densified pulp layer, and high basis weight nonwoven web made from continuous filaments or staple fibers with binder.

4. The absorbent article of claim 2, wherein said nesting ridge is composed of a heat set thermoplastic having sufficient stiffness to hold a garment elastic in place but not so stiff as to be noticeable or uncomfortable to wear.

5. The absorbent article of claim 2, wherein said stiffening means is composed of a material selected from the group consisting of foam materials, densified pulp, and nonwoven webs having bonding fiber or having latex bonding having sufficient stiffness to hold a garment elastic in place but not so stiff as to be noticeable or uncomfortable to wear.

6. The absorbent article of claim 2, further comprising two or three pairs of said garment-attachment nesting ridge pairs.

7. The absorbent article of claim 6, comprising three garment-attachment nesting ridge pairs.

* * * * *

UNITED STATES PATENT AND TRADEMARK OFFICE
CERTIFICATE OF CORRECTION

PATENT NO.      : 6,527,757 B1
DATED           : March 4, 2003
INVENTOR(S)     : Wanda W. Jackson It is certified that error appears in the above-identified patent and that said Letters Patent is hereby corrected as shown below:

<u>Column 12,</u>
Line 65, insert the following claims:

-- 8.  A method of positioning an absorbent article on an undergarment, comprising:
    (a) providing an absorbent configured to fit the pudendal region of a woman;
    (b) positioning a liquid-impermeable baffle on a bottom side of said absorbent;
    (c) providing a nesting ridge for receiving a crotch side surface of a crotch portion of an undergarment on a bottom side of said liquid-impermeable baffle to protect said undergarment from side leakage; and
    (d) providing stiffening means for holding said nesting ridges securely to said undergarment elastic edge.

-- 9.  The method of positioning an absorbent article on an undergarment as set forth in claim 8, further comprising positioning said nesting ridges to be not noticeable unless and until the wearer engage the nesting ridges as side protection elements.

--10.  The method of positioning an absorbent article on an undergarment as set forth in claim 9, further comprising protecting said crotch portion from side leakage around said absorbent.

--11.  The method of positioning an absorbent article on an undergarment as set forth in claim 9, further comprising guiding said crotch position into one pair of a plurality of said garment-attachment nesting ridge pairs.

Signed and Sealed this

Thirteenth Day of April, 2004

JON W. DUDAS
*Acting Director of the United States Patent and Trademark Office*